United States Patent [19]

Hagen et al.

[11] 4,324,793

[45] Apr. 13, 1982

[54] 4-NITRO-2-TRICHLOROMETHYLPHENYL DISULFIDES

[75] Inventors: Helmut Hagen, Frankenthal; Wolfgang Reuther, Heidelberg-Ziegelhausen; Ernst-Heinrich Pommer, Limburgerhof, all of Fed. Rep. of Germany

[73] Assignee: BASF Aktiengesellschaft, Fed. Rep. of Germany

[21] Appl. No.: 14,892

[22] Filed: Feb. 23, 1979

[30] Foreign Application Priority Data

Mar. 11, 1978 [DE] Fed. Rep. of Germany ....... 2810698

[51] Int. Cl.$^3$ .................. C07D 239/06; C07D 239/02
[52] U.S. Cl. ..................................... 424/270; 424/272; 424/244; 424/263; 424/273 R; 424/273 B; 548/132; 548/135; 548/166; 548/186; 548/221; 548/225; 548/251; 548/337; 544/315; 544/335; 546/290; 546/301; 548/341
[58] Field of Search ............... 424/273, 263, 270, 272, 424/267, 244; 260/305; 544/335, 315; 548/221, 337, 251, 217, 134, 135, 143, 182, 186, 225, 341, 166; 546/290, 301

[56] References Cited

U.S. PATENT DOCUMENTS

| | | | |
|---|---|---|---|
| 2,325,259 | 6/1962 | Mathes et al. | 548/186 |
| 2,922,790 | 1/1960 | Ruckett | 260/294.8 |
| 2,962,417 | 11/1960 | Harris | 167/30 |
| 3,555,158 | 1/1971 | Samuel et al. | 548/152 |
| 3,770,707 | 11/1973 | Boustany et al. | 260/306.5 |
| 4,049,665 | 9/1977 | Douglass | 260/294.8 |
| 4,061,645 | 12/1977 | Nüsslein et al. | 424/270 |
| 4,066,775 | 1/1978 | Pommer et al. | 424/270 |
| 4,083,986 | 4/1978 | Pommer et al. | 424/270 |

FOREIGN PATENT DOCUMENTS 48-98030 12/1973 Japan .

OTHER PUBLICATIONS

CA 81, 135720(c), 22237(g), 1974.
Chemical Week p. 63, Jun. 21, 1972.
Chemical Week p. 39, Jul. 26, 1972.
Farm Chemicals Handbook, p. D43, (1976).

*Primary Examiner*—Nicholas S. Rizzo
*Attorney, Agent, or Firm*—Keil & Witherspoon

[57] ABSTRACT

4-Nitro-2-trichloromethylphenyl disulfides, their manufacture, agents containing these compounds as active ingredients for use on microorganisms, and the use of these compounds for protecting substrates against microorganisms.

15 Claims, No Drawings

4-NITRO-2-TRICHLOROMETHYLPHENYL DISULFIDES

The present invention relates to new and valuable 4-nitro-2-trichloromethylphenyl disulfides having a microbiocidal, fungicidal and bactericidal action, processes for their manufacture, microbicides containing these compounds as active ingredients, and processes for combating fungi and bacteria with these compounds.

It is for example known to use N-(trichloromethylthio)-phthalimide (Chemical Week, June 21, 1972, p. 63), tetramethylthiuram disulfide (Chemical Week, July 26, 1972, p. 39) and 2-thiocyanomethylthiobenzothiazole (Farm Chemicals Handbook 1976, p. D43) as fungicides. However, their action is unsatisfactory.

It is an object of the present invention to provide new active ingredients and microbiocides having an improved action.

We have now found that 4-nitro-2-trichloromethylphenyl disulfides of the formula

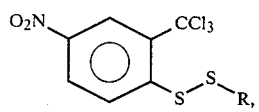  1 where R denotes a substituted or unsubstituted aliphatic radical of 1 to 16 carbon atoms, a substituted or unsubstituted araliphatic radical of a total of 7 to 9 carbon atoms, a substituted or unsubstituted mono- or polynuclear aromatic radical, or a substituted or unsubstituted 5- or 6-membered ring containing 1 to 3 oxygen, nitrogen or sulfur atoms as hetero atoms, or its benz homolog, have a better fungicidal action than the abovementioned prior art active ingredients.

Examples of suitable aliphatic radicals are linear or branched alkyl, optionally mono- or polysubstituted by carboxy, hydroxy, nitrile, amino, dialkylamino, alkoxy or carbalkoxy (each containing 1 to 3 carbon atoms in the alkyl), or by keto, such as methyl, ethyl, n- and isopropyl, n-butyl, n-hexyl, isooctyl, n-dodecyl, n-tridecyl, carboxymethyl, methoxyethyl, dimethylaminoethyl, aminoethyl, L-alanyl, carboxyethyl, acetyl, carbomethoxymethyl, hydroxyethyl or dicarboxyethyl.

Examples of suitable araliphatic radicals are benzyl or phenylethyl which may if desired be substituted 1 to 3 times in the phenyl by chloro, nitro and/or cyano, such as dichlorobenzyl and nitrobenzyl.

Examples of suitable aromatic radicals are benzene hydrocarbons, especially phenyl and naphthalene, which are optionally substituted 1 to 3 times by cyano, halogen (especially chloro) and/or nitro, e.g., cyanochlorophenyl, cyanonaphthyl, cyanonitrophenyl, chloronitrophenyl and cyanodichlorophenyl. These phenyl radicals may additionally bear a heterocyclic ring as substituent, e.g., imidazoline, methylimidazoline or tetrahydropyrimidine.

Suitable heterocyclic radicals for R are benzthiazole, benzimidazole, thiazole, imidazole, thiadiazole, oxazole, benzoxazole, oxdiazole or pyridyl, which may be substituted in the benzene ring 1 to 3 times by chloro, nitro and/or cyano, and/or in the heterocyclic ring by phenyl. Further heterocyclic radicals are thiazoline, imidazoline, 1,2,3,4-tetrazole and pyridine. Some of the heterocycles containing 5 ring members correspond to formula 1, where R denotes the radical

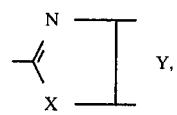

X denoting O, S or NH and Y denoting 2 hydrogen atoms, a double bond or fused phenyl.

Preferred meanings for R are alkyl of 2 to 12 carbon atoms optionally mono- or polysubstituted by carboxy, carbalkoxy, hydroxy, amino or keto; phenyl or naphthyl optionally substituted once or twice by chloro, cyano and/or nitro and/or a heterocyclic radical; thiazole or imidazoline optionally substituted by phenyl; and benzthiazole, benzimidazole and benzoxazole optionally substituted by chloro.

Examples of preferred meanings are n-butyl, isobutyl, n-dodecyl, tridecyl, carboxymethyl, phenyl, chlorophenyl, dichlorophenyl, chlorocyanophenyl, nitrophenyl, chloronitrophenyl, cyanonaphthyl, benzthiazolyl, chlorobenzthiazolyl, benzimidazolyl, thiazolyl, benzoxazolyl and 2-imidazolinylphenyl.

The compound 2-(4-nitro-2-trichloromethylphenyldithio)-1,3-benzthiazole is particularly preferred. It is particularly suitable for protecting wood against fungus attack and may be advantageously used in solvent-containing formulations.

The new active ingredients are especially suitable for protecting various materials against degradation or destruction by bacteria or fungi. Examples of materials which can be preserved or microbiocidally finished with the new active ingredients are glues and adhesives, plastics dispersions, emulsion paints, sealants, paper, textiles, leather, raw hides, plastics, especially soft PVC, rubber and wood. The compounds are also suitable as microbiocidal additives in cleansing agents and disinfectants, and as antislime agents in the paper industry.

The following microorganism for instance may be combated with the compounds according to the invention: *Chaetomium globosum, Chaetomium alba, Aspergillus terreus, Aspergillus niger, Aspergillus versicolor, Penicillium glaucum, Penicillium funiculosum, Trichoderma viride, Pullularia pullulans, Cladosporium herbarum, Cladosporium resinae, Humicola grisea, Glenospora graphii, Phoma violacea; Coniophora cerebella, Merulius lacrymans, Poria monticola, Lenzites trabea, Lenzites abietina, Trametes versicolor, Armillaria mellea; Streptomyces albus; Staphylococcus aureus, Escherichia coli, Pseudomonas aeruginosa, Aerobacter aerogenes,* and *Serratia marcescens.*

The agents containing 4-nitro-2-trichloromethylphenyl disulfides as active ingredients are generally suitable for protecting numerous substrates against attack by microorganisms and for combating microorganisms on or in substrates attacked by them.

A preferred application area is the preservation of wood, i.e. wood and wood-base materials, e.g., chipboard, against attack by microorganisms, and the combating of microorganisms which have attacked these substrates.

The compounds according to the invention are advantageously prepared by reaction of 4-nitro-2-trichloromethylbenzenesulfenyl chloride of the formula 2 with a compounds containing a mercapto group of the formula 3, in which R has the meanings given above for formula 1, in an inert solvent at from $-40°$ to $+120°$ C.

The reaction may be described by the following equation:

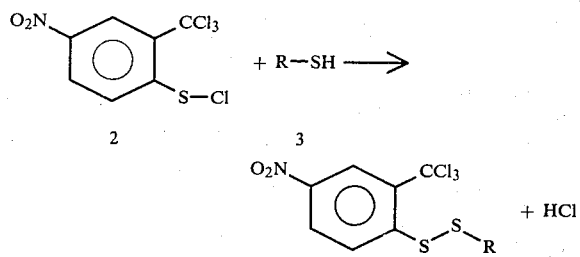

Examples of suitable inert solvents for the reaction are saturated aliphatic or cyclic ethers, such as diethyl ether, tetrahydrofuran, dioxane and dibutyl ether; aliphatic carboxylic acid esters, such as ethyl acetate and butyl acetate; lower alcohols, such as isobutanol; chlorinated hydrocarbons, such as methylene chloride; and aromatic hydrocarbons, such as benzene, toluene and xylene.

Of these solvents, diethyl ether, tetrahydrofuran, dibutyl ether, ethyl acetate, isobutanol and toluene are particularly preferred.

The preferred temperature range for the reaction is from $0°$ to $+60°$ C. Compounds containing a basic group in the radical R form the hydrochloride in the process according to the invention and may be obtained without difficulty as free base.

The 4-nitro-2-trichloromethylbenzenesulfenyl chloride used as starting compound is advantageously manufactured by the process disclosed in German Patent Application P 27 21 917.6 (corresponding to U.S. application Ser. No. 899,523, filed April 24, 1978, now U.S. Pat. No. 4,163,020) by chlorination of 5-nitrobenzo-1,2-dithio-3-thione in an inert solvent such as carbon tetrachloride, chloroform or dichloroethane, at from $-20°$ to $+100°$ C., preferably from $0°$ to $+50°$ C.

The following directions illustrate this process.

115 g of 5-nitrobenzo-1,2-dithio-3-thione is dispersed in 1,000 ml of carbon tetrachloride; at $10°$ C., 150 g of chlorine is then passed in. The reaction mixture is stirred for 12 hours at room temperature ($25°$ C). The solvent and sulfur chlorides are then distilled off under reduced pressure from a waterpump. The residue can be employed without further purification for synthesizing the disulfides according to the invention. Another possible route is to add 400 ml of diethyl ether to the residue, to filter and finally concentrate the ether solution, and to distil it under reduced pressure. 4-nitro-2-trichloromethylbenzenesulfenyl chloride is obtained at b.p. (1 mm Hg) $156°$ to $160°$ C. The compound has a melting point of $56°$ to $57°$ C. (recrystallized from ligroin).

The new active ingredients are applied as formulations. The present invention also relates to agents or formulations containing, in addition to conventional carriers and diluents, a compound of the formula 1.

The formulations, such as solutions, emulsions, suspensions, wettable powders, dusts, pastes and granules, are applied in known manner, e.g., after admixture with other agents, by painting, coating, impregnation, and other similar treatments. The formulations generally contain from 0.1 to 95, preferably 0.5 to 90, wt% of active ingredient. Application rates are, depending on the effect desired, from 0.001 to 5 wt%, based on the weight of the material to be protected, but preferably from 0.01 to 3 wt%.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The following list of bactericides and fungicides with which the compounds according to the invention can be combined is intended to illustrate the possible combinations, but the invention is in no way limited to these. Combination with other active ingredients often broadens the spectrum of microbiocidal action; with a number of these microbiocidal compositions synergistic effects also occur, i.e., the microbiocidal action of the composition is greater than the sum of the actions of the individual components.

Organotin compounds, such as tributyltin oxide and tributyltin benzoate, 2-bromo-2-nitro-1,3-propanediol, methylene bis-thiocyanate, chloroethylene bis-thiocyanate, formaldehyde, glutaraldehyde, chloroacetamide, N-methylolchloroacetamide, sodium dimethyl dithiocarbamate, zinc dimethyl dithiocarbamate, tetramethylthiuram disulfide, 1,6-bis-(4-chlorophenyl-diguanido)-hexane, alkyl trimethylammonium chloride, alkyl dimethylbenzylammonium chloride, cetylpyridinium chloride, dodecyl-di-(aminoethyl)-glycine, o-phenylphenol, p-chlor-m-cresol, chlorinated phenols, p-hydroxybenzoic acid ester, tetrachloroisophthalic acid dinitrile, halogenated salicylanilides, 2-halobenzanilide, N-cyclohexyl-N-methoxy-2,5-dimethylfuran-3-carboxamide, N,N-dimethyl-N'-phenyl-(N-fluorodichloromethylthio)-sulfamide, N-phenyl-N,N'-dimethyl-N'-fluorodichloromethylthiosulfonyl diamide, N-trichloromethylthiophthalimide, N-(1,1,2,2-tetrachloroethylthio)-tetrahydrophthalimide, benzimidazole-2-carbamic acid methyl ester, 2-(thiazolyl)-benzimidazole, 2-mercaptobenzthiazole, 2-thiocyanomethylthiobenzthiazole, benzisothioazolone, 2,5-dimethyltetrahydro-1,3,5-2H-thiadiazine-2-thione, and alkali metal and metal salts of N'-hydroxy-N-cyclohexyldiazenium oxide.

These active ingredients may be admixed with the compounds according to the invention in a weight ratio of from 1:10 to 10:1.

The active ingredients according to the invention also have a strong fungitoxic action on phytopathogenic fungi, especially from the Phycomycetes and Ascomycetes classes.

The new compounds are therefore suitable for instance for combating *Plasmopara viticola* in grapes, *Pseudoperonospora humuli* in hops, *Phytophthora infestans* in potatoes and tomatoes, *Septoria nodorum* in cereals, and *Venturia inaequalis* in apples. The fungicidal agents contain from 0.1 to 95% (wt%) of active ingredient, and preferably from 0.5 to 90%. Depending on the effect desired, application rates are from 0.1 to 3 kg of active ingredient per hectare.

The manufacture of the new active ingredients is illustrated in the examples which follow.

EXAMPLE 1

Butyldithio-4-nitro-2-trichloromethylbenzene

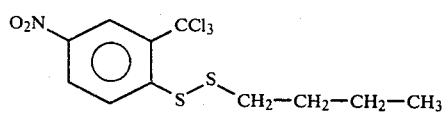

61 g of 4-nitro-2-trichloromethylbenzenesulfenyl chloride in 800 ml of diethyl ether is reacted in a stirred apparatus with 18 g of 1-butylmercaptan for 6 hours at 25° C. The completion of the reaction is determined by gas chromatography. After removal of the solvent, there is obtained 66 g (92% of theory) of (4-nitro-2-trichloromethylphenyl)-n-butyl disulfide as a yellow oil.

Elementary analysis:

|  | C | H | O | N | S | Cl |
|---|---|---|---|---|---|---|
| calc.: | 36.2 | 3.2 | 9.3 | 4.1 | 17.2 | 29.7 |
| found: | 36.6 | 3.3 | 8.9 | 3.9 | 17.8 | 29.5 |

EXAMPLE 2

Isopropyldithio-4-nitro-2-trichloromethylbenzene

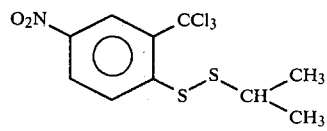

As in Example 1, 61 g of 4-nitro-2-trichloromethylbenzenesulfenyl chloride is reacted with 15 g of 2-propylmercaptan. There is obtained 63 g (91% of theory) of (4-nitro-2-trichloromethylphenyl)-isopropyl disulfide.

Analysis:

|  | C | H | O | N | S | Cl |
|---|---|---|---|---|---|---|
| calc.: | 34.2 | 2.8 | 9.5 | 4.1 | 18.2 | 30.5 |
| found: | 34.6 | 2.9 | 9.3 | 4.1 | 18.4 | 30.7 |

EXAMPLE 3 n-propyldithio-4-nitro-2-trichloromethylbenzene

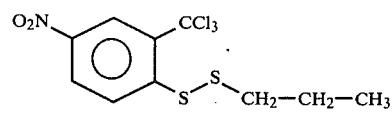

Similarly, 61 g of 4-nitro-2-trichloromethylbenzenesulfenyl chloride is reacted with 15 g of 1-propylmercaptan. There is obtained 62 g (89% of theory) of (4-nitro-2-trichloromethylphenyl)-n-propyl disulfide as a yellow oil.

Analysis:

|  | C | H | O | N | S | Cl |
|---|---|---|---|---|---|---|
| calc.: | 34.3 | 2.8 | 9.6 | 4.1 | 18.3 | 30.6 |
| found: | 34.6 | 2.9 | 9.3 | 4.1 | 18.4 | 30.7 |

EXAMPLE 4

3-chloro-2-cyanophenyldithio-4-nitro-2-trichloromethylbenzene

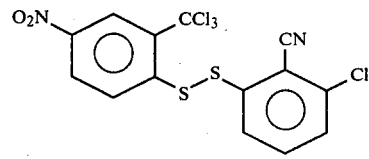

30.7 g of 4-nitro-2-trichloromethylbenzenesulfenyl chloride in 500 ml of diethyl ether is reacted in a stirred apparatus with 17 g of 2-cyano-3-chlorothiophenol for 4 hours at 30° C. There is obtained 38 g (86% of theory) of (4-nitro-2-trichloromethylphenyl)-(2-cyano-3-chlorophenyl)-disulfide; m.p.: 137° C.

Analysis:

|  | C | H | O | N | S | Cl |
|---|---|---|---|---|---|---|
| calc.: | 38.4 | 1.4 | 7.3 | 6.4 | 14.7 | 32.2 |
| found: | 38.2 | 1.4 | 7.3 | 6.4 | 14.6 | 32.3 |

EXAMPLE 5 n-dodecyldithio-4-nitro-2-trichloromethylbenzene

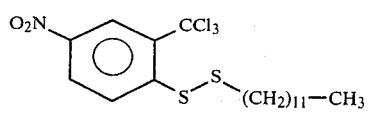

As in Example 1, 61.4 g of 4-nitro-2-trichloromethylbenzenesulfenyl chloride is reacted with 40.5 g of dodecyl-mercaptan. There is obtained 81 g (86% of theory) of (4-nitro-2-trichloromethylphenyl)-dodecyl disulfide. Analysis:

|  | C | H | O | N | S | Cl |
|---|---|---|---|---|---|---|
| calc.: | 48.8 | 6.2 | 6.9 | 2.7 | 13.4 | 21.8 |
| found: | 48.3 | 6.0 | 6.8 | 2.9 | 13.5 | 22.5 |

EXAMPLE 6

Carboxymethyldithio-4-nitro-2-trichloromethylbenzene

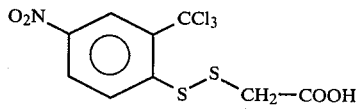

As in Example 1, 61.4 g of 4-nitro-2-trichloromethylbenzenesulfenyl chloride is reacted with 18.4 g of thioglycolic acid. After the solvent has been distilled off and the residue recrystallized from toluene, there is obtained 62 g of carboxymethyldithio-4-nitro-2-trichloromethylbenzene; m.p.: 140° C. Analysis:

|  | C | H | O | N | S | Cl |
|---|---|---|---|---|---|---|
| calc.: | 30.0 | 1.8 | 17.6 | 3.9 | 17.3 | 29.3 |
| found: | 29.8 | 1.7 | 17.6 | 3.9 | 17.6 | 29.3 |

EXAMPLE 7

2-(4-nitro-2-trichloromethylphenyldithio)-1,3-benzthiazole

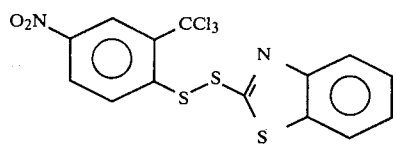

61.4 g of 4-nitro-2-dichloromethylbenzenesulfenyl chloride in 800 ml of isobutanol is reacted at 25° to 30° C. with 33.5 g of 2-mercaptobenzthiazole. There is obtained 84 g (96% of theory) of 2-(4-nitro-2-trichloromethylphenyldithio)-1,3-benzthiazole; m.p.: 97° C.
Analysis:

|  | C | H | O | N | S | Cl |
|---|---|---|---|---|---|---|
| calc. | 38.8 | 1.7 | 7.2 | 6.4 | 21.7 | 24.0 |
| found: | 38.4 | 1.6 | 7.3 | 6.4 | 21.9 | 24.3 |

EXAMPLE 8

Methyldithio-4-nitro-2-trichloromethylbenzene

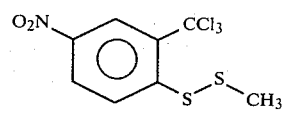

At 5° C., 7.2 g of methyl mercaptan is passed over a period of 20 minutes into a solution of 46 g of 4-nitro-2-trichloromethylbenzenesulfenyl chloride in 750 ml of diethyl ether. The reaction mixture is kept at 5° to 10° C. for 2 hours. After the solvent has been distilled off, the residue is recrystallized from ligroin. There is obtained 42 g (88% of theory) of methyldithio-4-nitro-2-trichloromethylbenzene; m.p.: 76° C.
Analysis:

|  | C | H | O | N | S | Cl |
|---|---|---|---|---|---|---|
| calc.: | 30.2 | 2.1 | 10.2 | 4.4 | 19.9 | 33.2 |
| found: | 30.1 | 1.9 | 10.0 | 4.4 | 20.1 | 33.4 |

EXAMPLE 9

2-(4-nitro-2-trichloromethylphenyldithio)-1-cyanonaphthalene

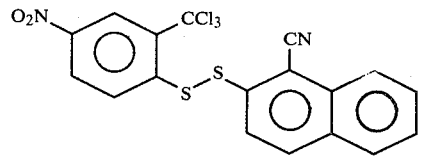

30.7 g of 4-nitro-2-trichloromethylbenzenesulfenyl chloride in 500 ml of dioxane is reacted with 18.5 g of 1-cyano-2-mercaptonaphthalene. There is obtained 37 g (81% of theory) of 2-(4-nitro-2-trichloromethylphenyldithio)-1-cyanonaphthalene; m.p.: 170° C. (recrystallized from toluene).
Analysis:

|  | C | H | O | N | S | Cl |
|---|---|---|---|---|---|---|
| calc.: | 47.2 | 2.0 | 7.6 | 6.2 | 13.7 | 23.2 |
| found: | 47.0 | 1.9 | 7.8 | 6.1 | 13.9 | 23.2 |

The following compounds were prepared as in Example 1:

EXAMPLE 10

(4-chloro-2-(2)-imidazolinylphenyl)-dithio-2-trichloromethyl-4-nitrobenzene

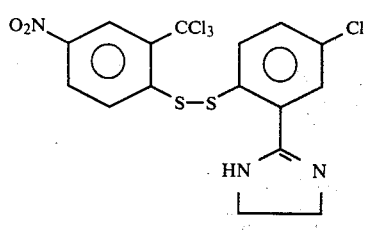
m.p.: 260° C.
(decomposes)

EXAMPLE 11

2-(1,3-benzimidazole)-dithio-4-nitro-2-trichloromethylbenzene

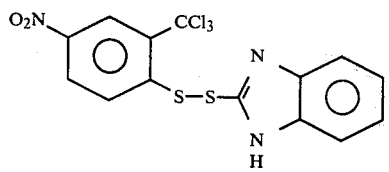
m.p.: 170° C.

EXAMPLE 12

[2-(5-methylimidazoline)-4-nitrophenyl-]-dithio-4-nitro-2-trichloromethylbenzene hydrochloride

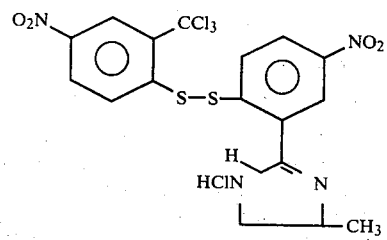
m.p.: 160° C.

EXAMPLE 13

[2-(tetrahydropyrimidinyl-)-4-chlorophenyl]-dithio-4-nitro-2-trichloromethylbenzene

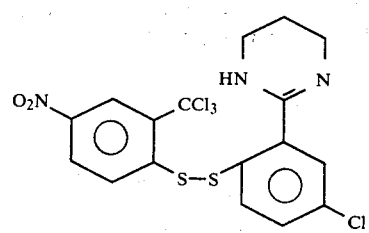
m.p.: 170° C.

EXAMPLE 14

1-phenyl-(1,2,3,4-tetrazole)-dithio-4-nitro-2-trichloromethylbenzene

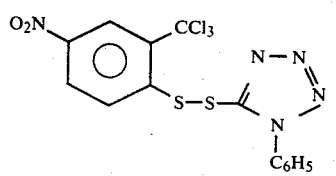
m.p.: 155° C.

EXAMPLE 15

1-acetyldithio-4-nitro-2-trichloromethylbenzene

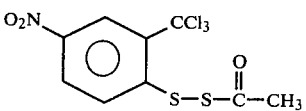
m.p.: 95° C.

EXAMPLE 16

2-(1,3-thiazoline)-dithio-4-nitro-2-trichloromethylbenzene

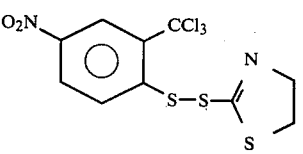
m.p.: 100° C.

EXAMPLE 17

2-aminoethyl-dithio-4-nitro-2-trichloromethylbenzene hydrochloride

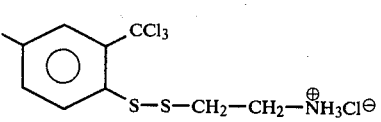
m.p.: 108° C.

EXAMPLE 18

2-(1,3-imidazoline)-dithio-4-nitro-2-trichloromethylbenzene hydrochloride

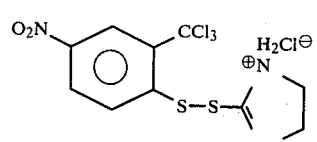
m.p.: 250° C.

EXAMPLE 19

3'-L-alaninedithio-4-nitro-2-trichloromethylbenzene m.p.: 175° C.

EXAMPLE 20

2-pyridinyldithio-4-nitro-2-trichloromethylbenzene m.p.: oil

EXAMPLE 21

2-carboxyethyldithio-4-nitro-2-trichloromethylbenzene

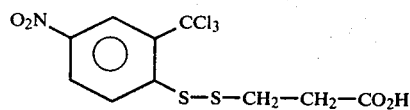

m.p.: oil

EXAMPLE 22 carbomethoxymethyldithio-4-nitro-2-trichloromethylbenzene

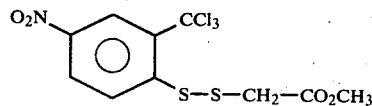

m.p.: oil

EXAMPLE 23

2-hydroxyethyldithio-4-nitro-2-trichloromethylbenzene

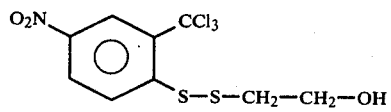

m.p.: 95° C.

EXAMPLE 24

1-(1,2-dicarboxyethyl)-dithio-4-nitro-2-trichloromethylbenzene

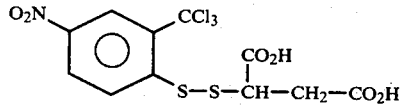

m.p.: 230° C.

EXAMPLE 25

2-(imidazolin-2-yl)-phenyldithio-2-trichloromethyl-4-nitrobenzyl hydrochloride

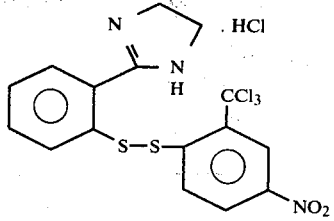

m.p.: 120–180° C. (decomposes)

The compound crystallizes with 2 moles of $CH_3OH$.

In the following examples, the action of compounds according to the invention is demonstrated and compared with the following 3 prior art agents:

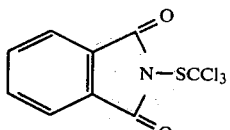 active ingredient 11

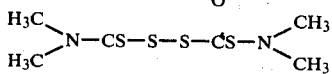 active ingredient 12

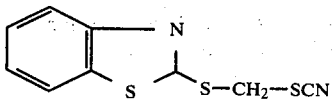 active ingredient 13

EXAMPLE 26

Fungicidal action on *Aspergillus niger*

The active ingredients are added to a nutrient solution ideally suited for promoting the growth of the fungus *Aspergillus niger*, in amounts of 100, 50, 25, 10, 5 and 1 parts by weight per million parts of nutrient solution. 20 ml lots of the nutrient solution treated in this manner are placed in 100 ml glass flasks and inoculated with 0.3 mg of Aspergillus spores. The flasks are incubated at 36° C. for 120 hours, and the extent of fungus spread—predominantly on the surface of the nutrient solution—is then assessed.

0 = no fungus growth, graduated down to

5 = uncontrolled fungus growth (surface of nutrient solution completely covered by fungus)

| Active ingredient no. | R= | ppm of active ingredient in nutrient solution | | | | | |
|---|---|---|---|---|---|---|---|
| | | 100 | 50 | 25 | 10 | 5 | 1 |
| 1 | —CH$_2$—CH$_3$ | 0 | 0 | 0 | 3 | 5 | 5 |
| 2 | —CH$_2$—CH$_2$—CH$_3$ | 0 | 0 | 0 | 3 | 5 | 5 |
| 3 | —CH(CH$_3$)$_2$ | 0 | 0 | 1 | 1 | 4 | 5 |
| 4 | —CH$_2$—CH$_2$—CH$_2$—CH$_3$ | 0 | 0 | 1 | 1 | 4 | 5 |
| 5 | —(CH$_2$)$_{11}$CH$_3$ | 0 | 0 | 1 | 3 | 5 | 5 |
| 6 | —CH$_2$—COOH | 0 | 0 | 1 | 3 | 5 | 5 |
| 7 | —⟨⟩—Cl | 0 | 0 | 0 | 1 | 3 | 5 |
| 8 | CN, Cl-phenyl | 0 | 0 | 0 | 0 | 0 | 1 |

-continued

| Active ingredient no. | 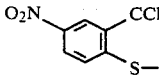 R= | ppm of active ingredient in nutrient solution | | | | | |
|---|---|---|---|---|---|---|---|
| | | 100 | 50 | 25 | 10 | 5 | 1 |
| 9 | 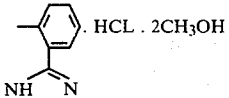 . HCL . 2CH₃OH | 0 | 0 | 0 | 1 | 3 | 5 |
| 10 | 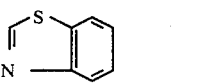 | 0 | 0 | 0 | 1 | 3 | 5 |
| 11 | prior art | 0 | 1 | 1 | 3 | 5 | 5 |
| 12 | prior art | 1 | 2 | 4 | 5 | 5 | 5 |
| 13 | prior art | 0 | 3 | 3 | 5 | 5 | 5 |

EXAMPLE 27

For the preparation of an oily wood preservative containing 2% of 2-(4-nitro-2-trichloromethylphenyl-dithio)-1,3-benzthiazole (active ingredient 10), 2 parts of the active ingredient is mixed with 15 parts of an alkyd resin having a medium content of oils (20% solid resin). Subsequently, 45 parts of a gasoline fraction containing aromatics is added, the mixture is, if desired, filtered to remove impurities, and a gasoline fraction containing aliphatics is added to make up to 100 parts.

EXAMPLE 28

2% oily wood preservatives are prepared analogously with active ingredients 2 and 8.

EXAMPLE 29

To determine the activity of the oily wood preservatives described in Examples 27 and 28 on the wood-destroying fungi *Coniophora cerebella* and *Trametes versicolor*, the procedure adopted was substantially in accordance with DIN No. 25, 176, Sheet 1, "Prüfung von Holzschutzmitteln, Mykologische Kurzprüfung (Klötzchenverfahren") (="Testing of wood preservatives, mycological short-term test (block process)"): pine sapwood blocks measuring 50×25×15 mm were coated at a rate of 200 g/m² of wood surface with oily wood preservative formulations. After the treated blocks had been stored for 4 weeks, they were placed, together with untreated blocks, in glass dishes containing the fungi *Coniophora cerebella* or *Trametes versicolor* in a nutrient agar. The dishes were then incubated in an atmospheric laboratory at 22° C. and a relative humidity of 70%. After 3 months, the fungus mycelium attaching to the blocks was removed and the blocks were dried. The degree of wood destruction was then ascertained in accordance with the scale given in the DIN specification.

| Treatment with formulations containing 2% of active ingredient | Degree of fungus attack after 3 months | |
|---|---|---|
| | Coniophora cerebella | Trametes versicolor |
| Active ingredient 2 | 1 | 1 |
| Active ingredient 8 | 1 | 1 |
| Active ingredient 10 | 1 | 1 |
| Control (only solvent, no active ingredient) | 3a/4b | 3b |

Assessment scale
1 undamaged
2a slight attack in parts
2b slight attack all over
3a heavy attack in parts
3b heavy attack all over
4a completely destroyed in parts
4b completely destroyed all over.

EXAMPLE 30

Bactericidal action on *Staphylococcus aureus* and *Escherichia coli*

Bacteria kill values were determined as follows. 5 ml of the water-diluted agents was placed in sterile test tubes and 5 ml of a doubly concentrated nutrient broth was admixed. The tubes were inoculated by adding one drop of 16-hour-old broth cultures (diluted 1:10) of the bacteria species *Staphylococcus aureas* and *Escherichia coli*; the tubes were then incubated for 24 hours at 37° C. Samples from the tubes were then transferred to bacteria culture media which were in turn incubated for 24 hours at 37° C. The dilution stage at which there was no bacterial growth after transfer of a sample to the nutrient medium is given as the kill.

| Active ingredient | Bactericidal action in dilution ratio | |
|---|---|---|
| | Staphylococcus aureus | Escherichia coli |
| 1 | 1:16,000 | 1:10,000 |
| 3 | 1:40,000 | 1:20,000 |
| 7 | 1:40,000 | 1:20,000 |
| 8 | 1:100,000 | 1:16,000 |
| 10 | 1:40,000 | 1:20,000 |
| 13 (prior art) | 1:16,000 | 1:8,000 |

EXAMPLE 31

Fungicidal action on Plasmopara viticola in grapes

Leaves of potted vines of the Müller-Thurgau variety are sprayed with aqueous suspensions containing (dry basis) 80% (wt%) of the active ingredient and 20% of sodium lignin sulfate. 0.05 and 0.025% (dry basis) spray liquors are used. After the sprayed-on liquor has dried, the leaves are infected with a zoospore suspension of *Plasmopara viticola*. The plants are first placed for 16 hours in a steam-saturated (moist) chamber at 20° C., and then in a greenhouse for 8 days at from 20° to 30° C. To accelerate and intensify the sporangiophore discharge, the plants are then again placed in the moist chamber for 16 hours. The extent of the disease is then assessed; 0 denotes no fungus attack, graduated down to 5, which denotes total attack (control).

| Active ingredient | Leaf attack after spraying with liquor containing active ingredients in amounts of | |
|---|---|---|
| | 0.05% | 0.025% |
| 1 | 0 | 0 |
| 2 | 0 | 0 |
| 3 | 0 | 3 |
| 6 | 0 | 0 |
| 7 | 0 | 0 |
| 9 | 0 | 0 |
| 10 | 0 | 0 |
| 11 (prior art) | 1 | 3 |
| 12 (prior art) | 2 | 4 |
| Control (untreated) | 5 | |

We claim:

1. A 4-nitro-2-trichloromethylphenyl disulfide of the formula $$O_2N-C_6H_3(CCl_3)-S-S-R$$

where R denotes a radical selected from Group I consisting of benzthiazole, benzimidazole, thiazole, imidazole, thiadiazole, oxazole, benzoxazole, oxdiazole, tetrazole and pyridyl, which Group I member may be substituted in the benzene ring 1 to 3 times by chloro, nitro and/or cyano, and/or in the heterocyclic ring by phenyl, or a radical selected from Group II consisting of thiazoline and imidazoline.

2. A process for the manufacture of compounds as defined in claim 1, wherein 4-nitro-2-trichloromethylbenzenesulfenyl chloride is reacted with a compound, containing a mercapto group, of the formula R-SH, where R has the meaning given in claim 1, in an inert solvent at from −40° to +120° C.

3. 2-(4-nitro-2-trichloromethylphenyldithio)-1,3-benzthiazole.

4. A compound as defined in claim 1, where R denotes $$-C\begin{pmatrix}N\\X\end{pmatrix}Y,$$

X denoting O, S or NH and Y denoting 2 hydrogen atoms, a double bond, or the divalent benzo radical.

5. (4-chloro-2-(2)-imidazolinylphenyl)-dithio-2-trichloromethyl-4-nitrobenzene.

6. 2-(1,3-Benzimidazole)-dithio-4-nitro-2-trichloromethylbenzene.

7. [2-(5-Methylimidazoline)-4-nitrophenyl-]-dithio-4-nitro-2-trichloromethylbenzene hydrochloride.

8. [2-(Tetrahydropyrimidinyl)-4-chlorophenyl]-dithio-4-nitro-2-trichloromethylbenzene.

9. 1-Phenyl-(1,2,3,4-tetrazole)-dithio-4-nitro-2-trichloromethylbenzene.

10. 2-(1,3-Thiazoline)-dithio-4-nitro-2-trichloromethylbenzene.

11. 2-(1,3-Imidazoline)-dithio-4-nitro-2-trichloromethylbenzene.

12. 2-Pyridinyldithio-4-nitro-2-trichloromethylbenzene.

13. 2-(Imidazolin-2-yl)-phenyldithio-2-trichloromethyl-4-nitrobenzyl hydrochloride.

14. A microbiocide composition containing, as active ingredient, a compound as defined in claim 1 and a carrier therefor.

15. A wood preservative composition containing, as active ingredient, 2-(4-nitro-2-trichloromethylphenyldithio)-1,3-benzthiazole and a carrier therefor.

* * * * *